US007694680B2

(12) United States Patent
Brichetto

(10) Patent No.: US 7,694,680 B2
(45) Date of Patent: Apr. 13, 2010

(54) AVIATOR EMERGENCY OXYGEN SYSTEM

(75) Inventor: David Brichetto, Las Vegas, NV (US)

(73) Assignee: Nevada Aviation Safety Consultants, Inc., Las Vegas, NV (US)

( * ) Notice: Subject to any disclaimer, the term of this patent is extended or adjusted under 35 U.S.C. 154(b) by 1182 days.

(21) Appl. No.: 11/164,202

(22) Filed: Nov. 14, 2005

(65) Prior Publication Data

US 2007/0107727 A1 May 17, 2007

(51) Int. Cl.
*A61M 11/00* (2006.01)

(52) U.S. Cl. ............................ 128/206.12; 128/204.18

(58) Field of Classification Search ............ 128/206.12, 128/200.28, 201.22, 201.18, 201.19, 200.27, 128/204.18, 207.17, 207.18, 201.24
See application file for complete search history.

(56) References Cited

U.S. PATENT DOCUMENTS 3,910,269 A * 10/1975 Ansite et al. ........... 128/201.24
4,660,555 A * 4/1987 Payton .................. 128/207.18
4,742,824 A * 5/1988 Payton et al. .......... 128/207.18
6,065,473 A * 5/2000 McCombs et al. ..... 128/204.18
6,247,470 B1 * 6/2001 Ketchedjian ........... 128/200.28
6,848,446 B2 * 2/2005 Noble ................... 128/207.18
6,886,559 B2 * 5/2005 McDonald et al. ..... 128/201.24
7,036,502 B2 * 5/2006 Manne .................. 128/200.28

* cited by examiner

*Primary Examiner*—Steven O Douglas
(74) *Attorney, Agent, or Firm*—Black Lowe & Graham PLLC

(57) ABSTRACT

A method, a system, and an oxygen delivery boomlet are configured to provide an additional partial pressure of oxygen to an aviator. The boomlet includes a conduit configured to receive an oxygen flow from a positive pressure oxygen source. A nozzle is in communicative connection with the conduit such that the oxygen flow the conduit receives is conducted to the nozzle. The nozzle is configured to direct the conducted flow of oxygen to an interpalatine region of the aviator. The boomlet is configured for attachment to a microphone boom.

25 Claims, 3 Drawing Sheets

AVIATOR EMERGENCY OXYGEN SYSTEM

FIELD OF THE INVENTION

This invention relates generally to Aviation Safety and, more specifically, to Aviation Environmental Safety.

BACKGROUND OF THE INVENTION

On Oct. 25, 1999, about 1213 central daylight time (CDT), a Learjet Model 35, N47BA, operated by Sunjet Aviation, Inc., of Sanford, Fla., crashed near Aberdeen, S. Dak. The airplane departed Orlando, Fla., for Dallas, Tex., about 0920 eastern daylight time (EDT). Radio contact with the flight was lost north of Gainesville, Fla., after air traffic control cleared the airplane to flight level 390. Several U.S. Air Force and Air National Guard aircraft intercepted the airplane as it proceeded northwest-bound.

The military pilots in a position to observe the accident airplane at close range stated (in interviews or via radio transmissions) that the forward windshields of the Learjet seemed to be frosted or covered with condensation. The military pilots could not see into the cabin. They did not observe any structural anomaly or other unusual condition. The military pilots observed the airplane depart controlled flight and spiral to the ground, impacting an open field. All occupants on board the airplane, the captain, first officer, and four passengers, were killed, and the airplane was destroyed. The National Transportation Safety Board determined the probable cause of this accident was incapacitation of the flight crewmembers because of their failure to receive supplemental oxygen following a loss of cabin pressurization, for undetermined reasons.

The airplane included an oxygen system that provided emergency oxygen for the flight crew and passengers comprising of a single oxygen bottle, an oxygen bottle pressure regulator with a shutoff valve, an oxygen pressure gauge, an overboard discharge relief valve and indicator, flight crew mask quick disconnect valves, flight crew masks, a manual passenger shutoff valve, an oxygen aneroid valve, an oxygen aneroid bypass shutoff valve, passenger oxygen actuator lanyard valves, and passenger masks. Oxygen was available to the flight crew at all times during the flight when the oxygen bottle pressure regulator shutoff valve is open, as it was at the time of impact.

If the pilots had received supplemental oxygen from the airplane's emergency oxygen system, they likely would have properly responded to the depressurization by descending the airplane to a safe altitude. Therefore, it appears that the partial pressure of oxygen in the cabin after the depressurization was insufficient for the flight crew to maintain consciousness and that the flight crewmembers did not receive any, or adequate, supplemental oxygen.

What is needed then, is a system, method, and apparatus for supplying a locally oxygen-rich environment during depressurization allowing flight crewmembers sufficient time to respond and to take corrective measures including the donning of an oxygen mask.

SUMMARY OF THE INVENTION

The present invention comprises a method, a system, and an oxygen delivery boomlet are configured to provide an additional partial pressure of oxygen to an aviator. The boomlet includes a conduit configured to receive an oxygen flow from a positive pressure oxygen source. A nozzle is in communicative connection with the conduit such that the oxygen flow the conduit receives is conducted to the nozzle. The nozzle is configured to direct the conducted flow of oxygen to an interpalatine region of the aviator. The boomlet is optionally configured for attachment to a microphone boom. Alternatively, the conduit is a void the microphone boom defines. The nozzle may optionally be attached to the microphone boom.

In accordance with further aspects of the invention, the positive pressure oxygen source includes a regulator. In an embodiment, the regulator includes an on/off valve.

In accordance with other aspects of the invention, the regulator is further configured to include a switch, the automated switch being configured to receive positive pressure from a first oxygen source in a first position and from a second oxygen source in a second position. The switch is, optionally, further configured to select the first position based upon the presence of a positive pressure from the first oxygen source or the second position based upon the presence of a positive pressure from the second oxygen source.

In accordance with still further aspects of the invention, the nozzle directs the flow to an interpalatine region, that region extending from generally an aviator's nostrils and extending to generally the aviator's mouth. Embodiments of the invention direct the oxygen flow to the nostrils particularly while other embodiments direct the oxygen flow to the interpalatine region generally midway between the nostrils and the mouth.

As will be readily appreciated from the foregoing summary, the invention provides a system, method, and apparatus for supplying a locally oxygen-rich environment during depressurization allowing flight crewmembers sufficient time to respond and to take corrective measures including the donning of an oxygen mask.

BRIEF DESCRIPTION OF THE DRAWINGS

Preferred and alternative embodiments of the present invention are described in detail below with reference to the following drawings.

DETAILED DESCRIPTION OF THE PREFERRED EMBODIMENT

The present invention comprises a method, a system, and an oxygen delivery boomlet are configured to provide an additional partial pressure of oxygen to an aviator. The boomlet includes a conduit configured to receive an oxygen flow from a positive pressure oxygen source. A nozzle is in communicative connection with the conduit such that the oxygen flow the conduit receives is conducted to the nozzle. The nozzle is configured to direct the conducted flow of oxygen to an interpalatine region of the aviator. The boomlet is configured for attachment to a microphone boom.

Figure 1:
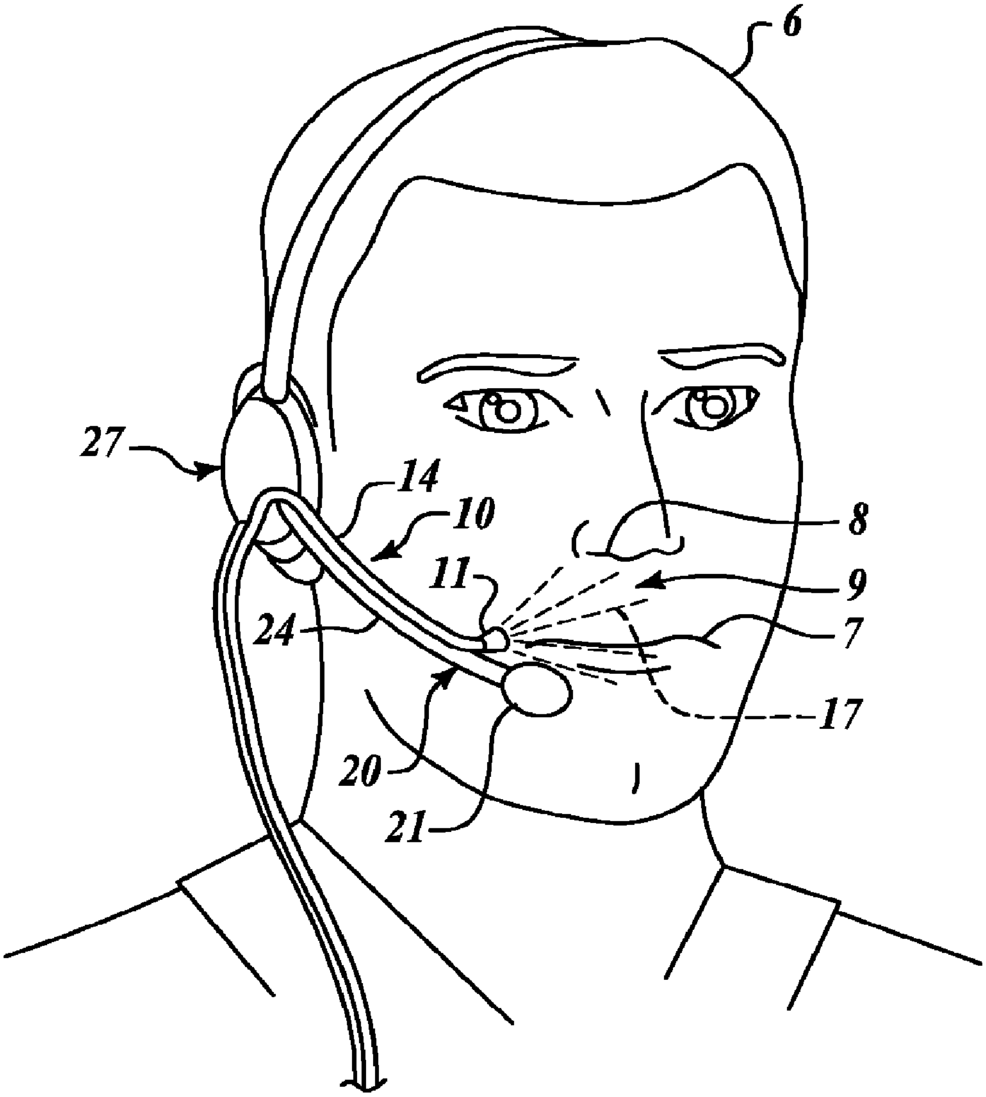
FIG. 1 is a perspective view of an embodiment of an boomlet.

Referring to FIG. 1, a boomlet 10 is attached to a headset assembly 27. The headset assembly 27 is of the sort commonly used by an aviator 6 to maintain radio contact with air traffic control (ATC) functions while engaged in piloting an aircraft. Such a headset assembly 27 generally includes a microphone boom assembly 20, itself consisting of a microphone 21 on a microphone boom 24. The microphone boom 24 is used to place the microphone 21 in advantageous proximity to a mouth 7 of the aviator 6 in order to capture pressure variations that are the sound of uttered words.

Extending between the mouth 7 and nostrils 8, an aviator 6 has an interpalatine region 9. The interpalatine region includes the nostrils 8 and the mouth at opposed boundaries. It is advantageous to direct an oxygen flow 17 at this interpalatine region 9 in order to increase the oxygen concentration the aviator 6 is capable of inhaling at times of rapid cabin depressurization.

The boomlet 10 is configured to direct oxygen at the interpalatine region 9 by directing the oxygen flow 17 through a nozzle 11, the nozzle 11 being configured to vent oxygen under pressure to generate and direct the oxygen flow 17. The oxygen under pressure is provided the nozzle 11 through a conduit 14 that, itself, is connected both to the nozzle 11 and at an opposed end to an airplane oxygen system.

The airplane oxygen system provides emergency oxygen for the aviator 6. Generally oxygen is available to the aviator 6 automatically above 14,000±750 feet cabin altitude or manually (at any cabin altitude) by opening the normally closed oxygen aneroid bypass shutoff valve, which is located on an instrument sidewall (not shown). The boomlet 10 provides the oxygen without requiring the aviator 6 to don a mask. In the course of an unplanned or undetected loss of cabin pressure, the aviator 6 will have a sufficient oxygen flow 17 to make such maneuvers as are necessary to respond to the loss of cabin pressure without having to interrupt the maneuvers to don the mask.

By way of nonlimiting example, the boomlet 10 is shown attached to the microphone boom 24 advantageously providing a mounting site for the nozzle 11 allowing the directing of the oxygen flow 17 at the interpalatine region 9. While so attaching the boomlet 10 to the microphone boom 24 is a means of properly positioning the nozzle 11, another embodiment includes the incorporation of the boomlet 10 into the microphone boom 24. A void that the microphone boom 24 defines within its length suitable serves as a portion of the conduit 14 thereby advantageously fixing a spatial relationship between the nozzle 11 and the microphone 21. The spatial relationship is chosen to prevent the oxygen flow from obscuring sounds the microphone is configured to capture.

In another embodiment, the nozzle 11 is configured to be a nasal cannula inserted into or in close proximity to the nostrils 8. Advantageously, a nasal cannula nozzle 11 provides further concentration of oxygen in the ambient gasses available to the nostrils 8 of the aviator 6. By way of non-limiting example, the nasal cannula nozzle 11 might optionally include a valve opening the cannula nozzle 11 to the ambient atmosphere when no relative oxygen pressure is supplied by the conduit 14 but closing the cannula to the ambient atmosphere when the conduit 14 supplies oxygen pressure to vent generating an oxygen flow 17 into the nostrils 8.

Figure 2:
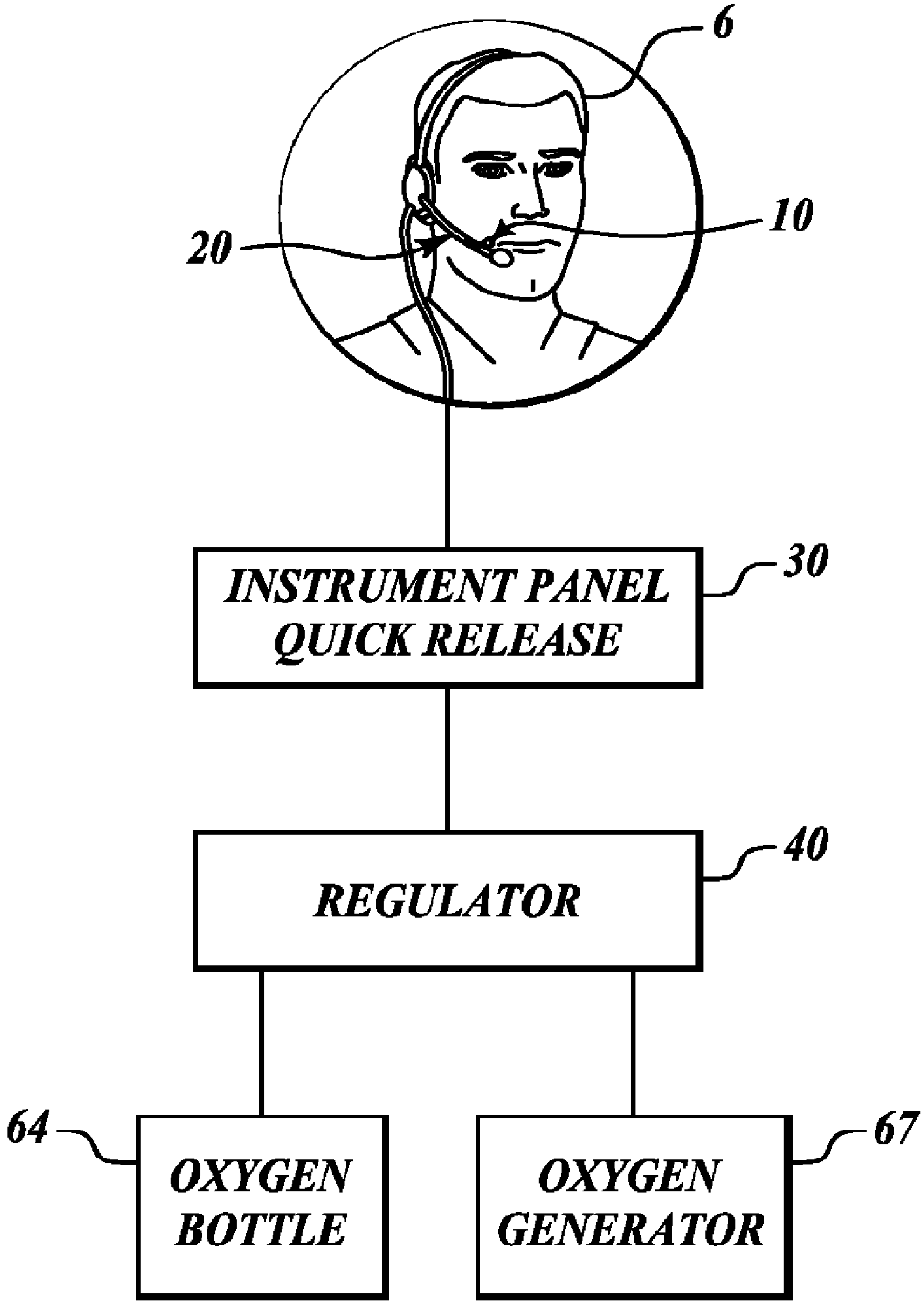
FIG. 2 is a block diagram of a system for providing oxygen for supplying a locally oxygen-rich in an aviator's interpalatine region.

Referring to FIG. 2, the boomlet 10, including the conduit 14 is detachably attached to an instrument panel quick release 30. While not limited to placement on the instrument panel, the instrument panel quick release 30 as used herein refers to any suitable quick release of the sort used to allow the aviator 6 to join the boomlet 10 by means of its conduit 14 to the oxygen supply system of an aircraft. Quick releases are known to the aviation oxygen industry and readily obtained from suppliers. The instrument panel quick release 30 is not necessary for any embodiment of the invention but, rather, is provided for the convenience of the aviator 6.

A regulator 40 is provided to step down oxygen pressure to provide a breathable oxygen flow 17. By way of explanation, a typical oxygen bottle 64 has a storage capacity of 38 cubic feet at 1,800 pounds per square inch (psi). Oxygen pressure for the flight crew and passenger distribution systems is reduced to 70 psi via the oxygen bottle pressure regulator/shutoff valve that is mounted directly on the oxygen bottle 64 and is included therein in FIG. 2 for purposes of clarity. The oxygen bottle 64 and attached oxygen bottle pressure regulator/shutoff valve are generally located in the nose cone of the airplane and are inaccessible to the flight crew during flight and the 70 psi pressure lines convey oxygen to the aviator at an advantageous flow rate. Nonetheless, venting a 70 psi pressure will result in too great a volume at too great a velocity to allow the aviator 6 to comfortably breathe. The regulator 40 further steps down the pressure from the 70 psi pressure lines. Additionally, the regulator 40 allows for a second oxygen supply, in the shown embodiment in FIG. 2, in this case, oxygen supplied by an oxygen generator 67.

Figure 3:
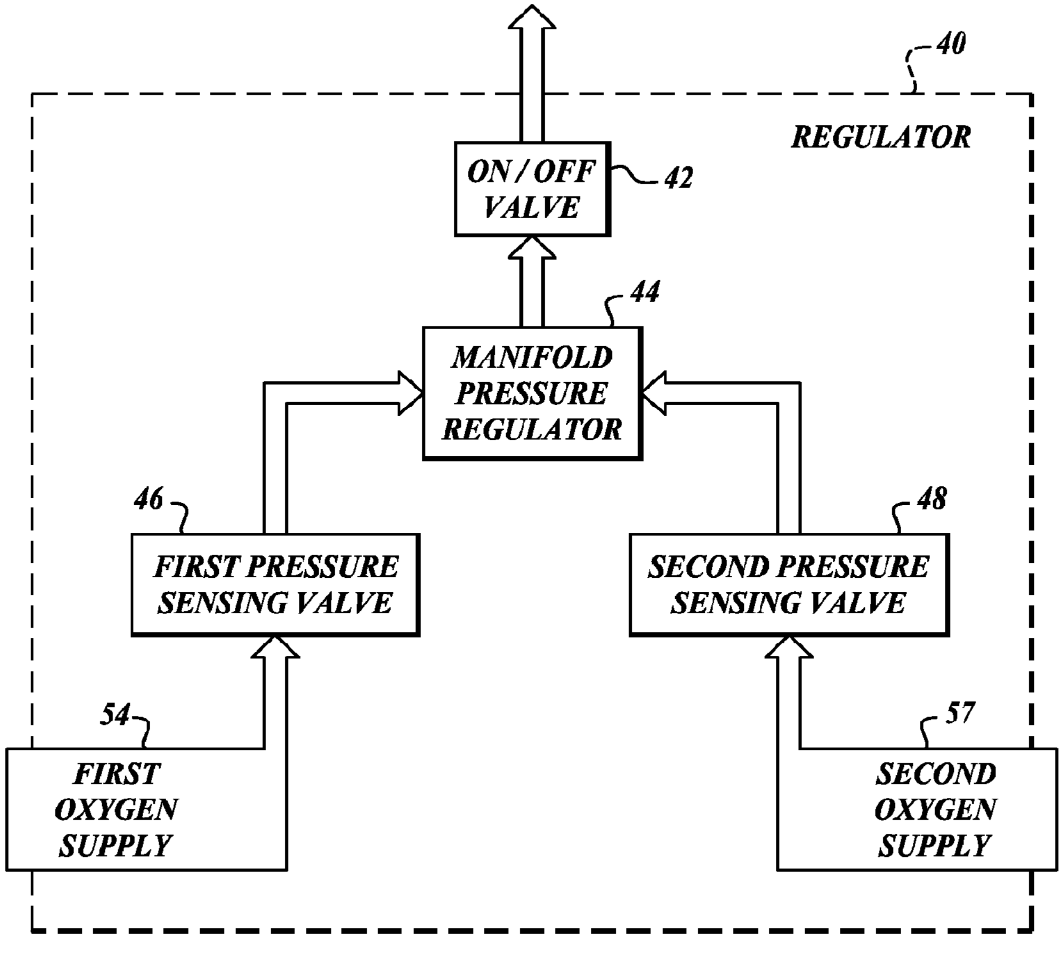
FIG. 3 is a block diagram of a regulator apparatus.

Referring to FIG. 3, the regulator 40 in one nonlimiting embodiment is configured to allow redundancy in the provision of oxygen and includes an on/off valve 42; a manifold pressure regulator 44; a first pressure sensing valve 46; and a second pressure sensing valve 48. The pressure sensing valves 46, 48, are configured to prevent contamination or escape of the oxygen flow 17 while allowing oxygen from a first oxygen supply 54, such as the oxygen bottle 64 (FIG. 2), and from a second oxygen supply 57, such as the oxygen generator 67 (FIG. 2) to be selectably provided to the on/off valve 42 to supply the boomlet 10 (FIGS. 1, 2). Each of the first and second pressure sensing valves 46, 48 tests continually for the presence of a relative oxygen pressure and if it is absent, shuts down the pressure sensing valves 46, 48 according to that absence assuring a ready source of relative oxygen pressure.

At the manifold pressure regulator 44 the flows are selectably chosen to give a reliable oxygen flow 17 (FIG. 1) at the nozzle 11. This can be by any of several means. Pneumatic switching, electronic switching, or a combination of electronic and pneumatic means will selectably choose the preferred source. Generally speaking, for example, exhausting oxygen from the oxygen bottle 64 (FIG. 2) is less expensive than activating and exhausting the oxygen from the oxygen generator 67 (FIG. 2). The switching within the manifold regulator 44 will accommodate the appropriate and reliable supply of an oxygen flow 17 at the nozzle 11.

Commercially available regulators include the on/off valve 42, such as the Puritan Bennett™ part number 112145A, having three positions (NORMAL, 100%, and EMERGENCY) and incorporates a dilution aneroid that will progressively shut off the diluter (cabin) port upon rising cabin altitudes, thereby supplying 100 percent oxygen at cabin altitudes above 33,000 feet. When the selector lever is in the EMERGENCY position, the regulator supplies 100 percent oxygen, regardless of altitude, at a positive pressure of approximately 0.15 psi. This regulator will also automatically supply oxygen under positive pressure (approximately 130 liters per minute at 0.5 psi) at cabin altitudes above 39,000 feet, regardless of the regulator-selected mode. In this non-limiting embodiment of the invention, the on/off valve is similarly operative.

While the preferred embodiment of the invention has been illustrated and described, as noted above, many changes can be made without departing from the spirit and scope of the invention. For example, the conduit 14 need not be attached to the microphone boom 24 so long as the nozzle 11 is suitably configured to provide the oxygen flow 17 at the interpalatine region 9. Accordingly, the scope of the invention is not limited by the disclosure of the preferred embodiment. Instead, the invention should be determined entirely by reference to the claims that follow.

The invention claimed is:

1. An oxygen delivery boomlet to provide an additional partial pressure of oxygen to an aviator, the boomlet comprising:

a conduit configured to receive an oxygen flow from a positive pressure oxygen source;

the positive pressure oxygen source being configured to supply oxygen upon a rapid depressurization of a cabin enclosing an aviator; and a nozzle in communicative connection with the conduit such that the oxygen flow the conduit receives is conducted to the nozzle, the nozzle being configured to direct the conducted flow of oxygen to nostrils of the aviator.

2. The boomlet of claim 1, wherein the boomlet is configured for attachment to a microphone boom.

3. The boomlet of claim 1, wherein the nozzle is attached to the microphone boom.

4. The boomlet of claim 1, wherein the positive pressure oxygen source includes a regulator.

5. The boomlet of claim 4, wherein the regulator includes an on/off valve.

6. The boomlet of claim 4, wherein the regulator is further configured to include a switch, the automated switch being configured to receive positive pressure from a first oxygen source in a first position and from a second oxygen source in a second position.

7. The boomlet of claim 6, wherein the switch is further configured to select the first position based upon the presence of a positive pressure from the first oxygen source or the second position based upon the presence of a positive pressure from the second oxygen source.

8. The boomlet of claim 1, wherein the nostrils are located in an interpalatine region and wherein the oxygen flow is directed at the interpalatine region.

9. A method for providing an oxygen flow to an aviator's nostrils, the method comprising:

sensing a rapid depressurization in a cabin enclosing the aviator, receiving a positive pressure of oxygen from an oxygen source, in response to the rapid depressurization in the cabin;

venting the positive pressure of oxygen to generate a flow of oxygen; and directing the flow of oxygen through a nozzle to the interpalatine region.

10. The method of claim 9, wherein the directing the flow to the interpalatine region includes directing the flow to the nostrils.

11. The method of claim 9, wherein the receiving the positive pressure includes receiving the positive pressure from an oxygen source.

12. The method of claim 11, wherein the oxygen source includes a regulator.

13. The method of claim 12, wherein the regulator includes an on/off valve.

14. The method of claim 12, wherein the regulator is further configured to include a switch, the automated switch being configured to receive positive pressure from a first oxygen source in a first position and from a second oxygen source in a second position.

15. The method of claim 14, wherein the switch is further configured to select the first position based upon the presence of a positive pressure from the first oxygen source or the second position based upon the presence of a positive pressure from the second oxygen source.

16. The method of claim 9, wherein the venting includes conducting the flow of oxygen through a conduit.

17. The method of claim 16, wherein the conduit is configured for attachment to a microphone boom.

18. A system for providing an oxygen flow to an aviator's nostrils, the method comprising:

A conduit configured to receive a positive pressure of oxygen from an oxygen source, the oxygen source being triggered by a rapid depressurization in a cabin enclosing the aviator; and A nozzle configured to, vent the positive pressure of oxygen to generate a flow of oxygen to the nostrils.

19. The system of claim 18, wherein the nozzle configured to direct the flow to the interpalatine region is further configured to direct the flow to the nostrils.

20. The system of claim 18, wherein the conduit is configured to receive the positive pressure from an oxygen source.

21. The system of claim 20, wherein the oxygen source includes a regulator.

22. The system of claim 21, wherein the regulator includes an on/off valve.

23. The system of claim 21, wherein the regulator is further configured to include a switch, the automated switch being configured to receive positive pressure from a first oxygen source in a first position and from a second oxygen source in a second position.

24. The system of claim 21, wherein the switch is further configured to select the first position based upon the presence of a positive pressure from the first oxygen source or the second position based upon the presence of a positive pressure from the second oxygen source.

25. The system of claim 18, wherein the conduit is configured for attachment to a microphone boom.

* * * * *